United States Patent [19]

Winthrop et al.

[11] Patent Number: 5,868,132
[45] Date of Patent: Feb. 9, 1999

[54] ENDOTRACHEAL TUBE HOLDER

[76] Inventors: Neil Winthrop, 134 Sevilla Ave., Royal Palm Beach, Fla. 33411; Harry Bayron, 7439 Pioneer Rd., West Palm Beach, Fla. 33413

[21] Appl. No.: 858,028

[22] Filed: May 16, 1997

[51] Int. Cl.⁶ .................................................. A61M 16/00
[52] U.S. Cl. .............................. 128/207.14; 128/207.17; 128/911; 128/DIG. 26
[58] Field of Search ....................... 128/207.14, DIG. 26, 128/912, 911, 207.17; 606/156, 157; 604/174, 179, 180

[56] References Cited

U.S. PATENT DOCUMENTS

| | | | |
|---|---|---|---|
| 3,924,636 | 12/1975 | Addison . | |
| 3,927,676 | 12/1975 | Schultz . | |
| 4,331,143 | 5/1982 | Foster | 128/207.14 |
| 4,460,356 | 7/1984 | Moseley . | |
| 4,683,882 | 8/1987 | Laird . | |
| 4,744,358 | 5/1988 | McGinnis | 128/67.17 |
| 4,844,061 | 7/1989 | Carroll | 128/207.17 |
| 4,906,234 | 3/1990 | Voychehovski | 128/207.17 |
| 5,076,269 | 12/1991 | Austin | 128/207.14 |
| 5,306,233 | 4/1994 | Glover . | |
| 5,308,339 | 5/1994 | Kalt et al. | 604/180 |
| 5,448,985 | 9/1995 | Byrd . | |
| 5,490,504 | 2/1996 | Vrona . | |
| 5,501,216 | 3/1996 | Byrd . | |
| 5,653,232 | 8/1997 | Rogers et al. | 128/207.14 |

*Primary Examiner*—John G. Weiss
*Assistant Examiner*—V. Srivastava
*Attorney, Agent, or Firm*—McHale & Slavin

[57] ABSTRACT

An endotracheal tube holding device for holding a tube inserted into a patient's mouth and into the trachea. The tube is held in position by the device which has been adhesively secured to the patient's face by a foam strip with an adhesive backing to comfortably, yet securely attach the holding device. The strip is arcuate-shaped and positioned along the upper lip and attached on each end to the patient's cheeks. A support fixture with a lipped support tab extends therefrom and is attached to the foam strip. An adhesive tape strip extends from each side of the support tab and wraps around the positioned ETT. The lip prevents the tape strip from slipping off the support tab thereby providing a secure attachment of the ETT to the support fixture. An accessory port may be included in the support holder to allow for insertion of items above or below the ETT tube without removal of the device from the patient's face.

19 Claims, 3 Drawing Sheets

ENDOTRACHEAL TUBE HOLDER

FIELD OF INVENTION

This invention relates to an endotracheal tube (ETT) and, in particular, to an improved ETT holder which adhesively attaches to a patient's skin.

BACKGROUND OF THE INVENTION

An endotracheal tube (ETT) is often used in the medical profession to provide a direct pathway for air, oxygen, or other such gases into a patient's lungs. The ETT is inserted through a patients mouth and is positioned in the trachea a certain distance. As a result, a patient's lungs can be supplied with gas from a ventilator. Moreover, an ETT is often necessary when a patient is not spontaneously breathing in order to properly move gas into the lungs.

Upon insertion, an ETT will likely not stay in position due to various intervening factors. Such factors include back pressure from the ETT and the lungs which tends to expel the ETT. Another frequent occurrence is patient movements which tends to move or dislodge the ETT from its optimum position. If the ETT becomes dislodged, the patient's life can be endangered due to the lack of gas being supplied to the patient.

Accordingly, a number of devices have been developed which serve to hold an ETT in position. U.S. Pat. Nos. 3,927,676; 5,306,233; 5,448,985; 5,490,504 and 5,501,216 each disclose devices for securing an endotracheal tube. However, each of these devices uses a strap which wraps around the patient's head or neck. Such straps can be hard to install and are uncomfortable for the patient.

U.S. Pat. No. 3,924,636 discloses an ETT holder which attaches to the patient's face via a facial strip with a central opening. This strip encompasses the patient's entire mouth. A tube-attaching strap is used to wrap around the ETT and is permanently attached to the bottom of a tube support. The tube support, however, is narrow-based and thereby does not adequately distribute stresses across the facial strip. The facial strip also encompasses the patient's mouth, a feature that will likely cause discomfort to the patient. Further, the permanent tube-attachment strap allows little relative movement of the inserted ETT against the tube support which can also cause further patient discomfort. U.S. Pat. No. 4,683,882 also discloses an ETT holder which poses similar problems having an adhesive facial attachment strip and a permanently attached C-clamp or notched strap clamp for attaching the ETT.

Still other types of attachments include U.S. Pat. No. 4,460,356, which disclose a pre-cut anchor tape with an upper and lower portion for securing an intravenous catheter to the arm of a person. The tape strip is adhered to the person along an upper portion, and a lower portion wrapped around a catheter running over the tape. U.S. Pat. No. 5,308,339 discloses a universal clamp for holding an article to an object. The clamp includes a base strip which is secured to an object and a releasably attached flap is placed over the article to hold it to the base strip.

Accordingly, the known prior art does not disclose an easy to use ETT holder which will securely and yet comfortably hold an ETT inserted into the patient. What is needed in the field is an ETT holder which securely attaches to the patient's face, yet minimizes contact area and related discomfort for the patient. Also a device is needed with a wider-based support structure for attaching the ETT, thereby more adequately distributing motion stresses across the holder. The device provides firm securement of the ETT inside the patient, allows for patient movement, is comfort to the patient, and allows for quick detachment of the ETT for repositioning if necessary.

SUMMARY OF THE INVENTION

The present invention provides an apparatus for holding an endotracheal tube (ETT) in position once it has been inserted and positioned inside of a patient. The apparatus is comprised of a foam strip with a medical grade adhesive backing, with the adhesive being covered by protective peel-off stripe. The front of the foam strip includes a support fixture adhered along the bottom edge. The fixture is preferably formed from a flexible plastic. The fixture includes an arcuate-shaped support tab extending away from the foam strip along the bottom edge of the fixture. The arcuate support tab includes a tab lip extending upward along its outermost edge. A strip of adhesive tape is placed over the upper portion of the support tab with the adhesive surface facing downward and extending from both sides of the support tab. The tape strip is oriented with its adhesive side facing downward and protectively covered by peel away strips. The tape strip is also contained from slipping off of the support tab by a proximal and distal tab lip. However, in an emergency, the ETT can be quickly removed by forcing the tape strip over the lip and off of the support tab, or by cutting away the tape strip. While the tape strip is preferred, the strip may be made from a hook & pile "VELCRO" attachment strip, adjustable hose style clamp strip, a tie strap, and so forth, all of which is deemed within the scope of this invention.

In operation, the protective strip is removed from the adhesive backing on the foam strip and the foam strip is adhered to the patient's face. The strip is positioned so that it runs from cheek to cheek and under the patient's nose. To accommodate such positioning, the strip is shaped so that it is relatively narrower in the middle and wider at the ends, similar in shape to a bow-tie. The wider ends provide a larger area for the device to adhere to the cheeks, thereby providing a more secure and stable platform for holding the ETT. Once the ETT tube is properly positioned, the attached support fixture and arcuate support tab are oriented along the upper, or lower, lip of the patient. The tube is positioned so that it rests inside the arcuate cavity formed on the underside of the support tab. The arcuate shape of the support tab allows the tab to substantially conform to the shape of ETT tube. The support tab may include additional accessory apertures allowing for the positioning of nasal and oral gastric tubes in addition to the ETT.

The adhesive surface on the tape strips are exposed by peeling off the protective coverings and the strips are adhesively wrapped around the ETT tube and any accessory tubes. The ETT tube is thereby secured to the holding apparatus in a proper position to service the patient, with the tab extension and support fixture particularly providing a stable anchoring surface for the ETT, as well as nasal gastric, oral gastric, or the like tubes.

Thus, it is an object of the present invention to provide a holder which securely holds an ETT or other such oral tube in position while it is being used on a patient.

It is still another object of the present invention to provide a holder which uses an attachment device which comfortably and securely adheres to the face of a patient.

It is yet another object of the present invention to provide a holder with an attachment device comprised of an adhesive foam strip with peel off protective covering strips over the adhesive backing.

It is still another object of the present invention to provide a tabbed support fixture connected to the front of the attachment device with adhesively backed tape strips extending therefrom for securely attaching the ETT tube in position.

It is yet another object of the present invention to provide a method of using the ETT holder whereby the foam strip is attached to the patient's face and the tape strips are wrapped around the ETT when positioned inside the patient.

Still another object of the present invention is to teach the use of an optional accessory port for inclusion in the support holder to allow for insertion of items such as an oral or nasal gastric tube above and/or below the ETT tube without removal of the holder device from the patient's face and utilizing the tape strips to secure them.

Other objects and advantages of this invention will become apparent from the following description taken in conjunction with the accompanying drawings wherein are set forth, by way of illustration and example, certain embodiments of this invention.

DETAILED DESCRIPTION OF THE PREFERRED EMBODIMENT

Although the invention will be described in terms of a specific embodiment, it will be readily apparent to those skilled in this art that various modifications, rearrangements and substitutions can be made without departing from the spirit of the invention. The scope of the invention is defined by the claims appended hereto.

Figure 1:
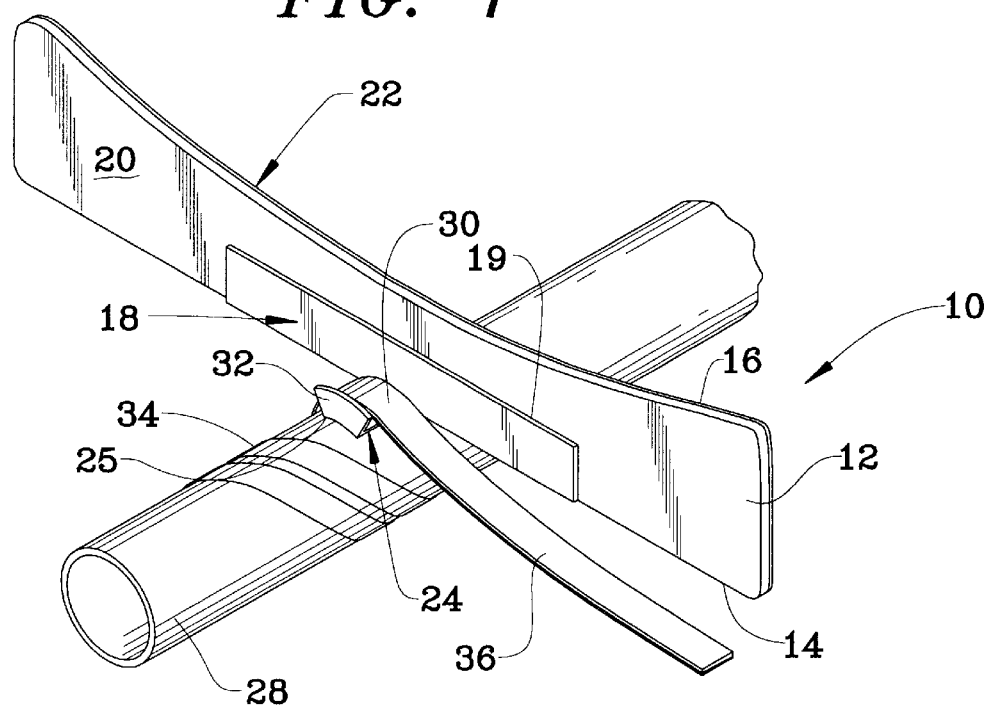
FIG. 1 is a perspective view of the ETT holder of the instant invention.
Figure 2:
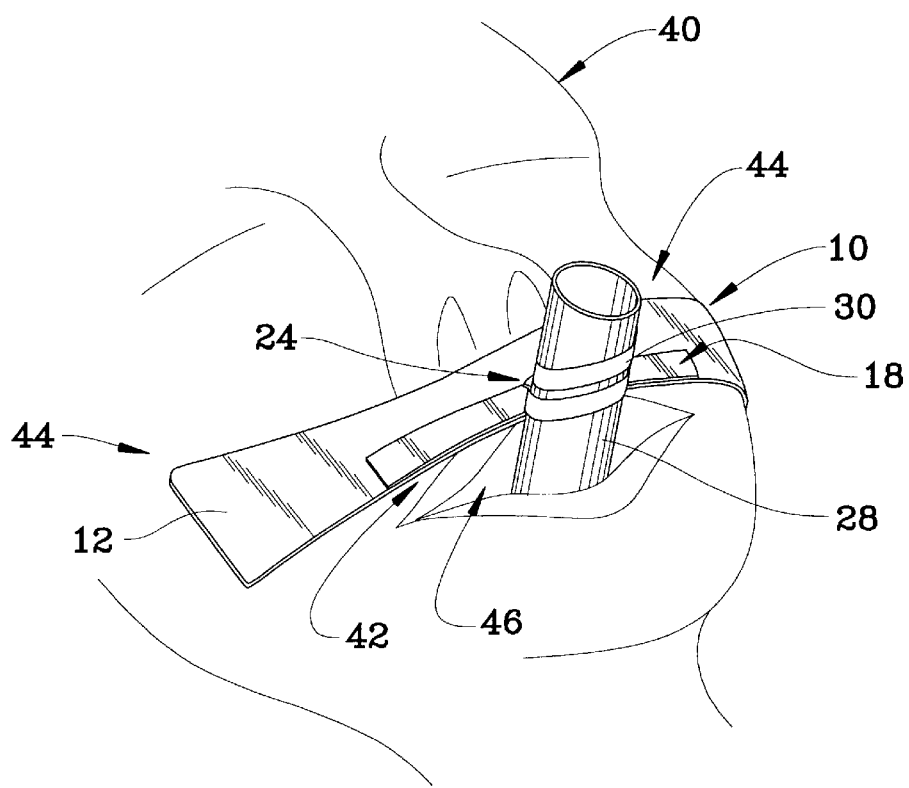
FIG. 2 is a pictorial view of the ETT holder as used on a patient.

Referring now to FIGS. 1–2, a perspective view of the ETT holder 10 is shown. A foam strip 12 includes a straight bottom edge 14 and an arcuate shaped upper edge 16. The foam strip 12 includes a front surface 20 and an adhesively backed rear surface 22. A support fixture 18 is adhesively mounted, via glue or other such substance, to the front surface 20 of the foam strip 12 along the center of the bottom edge 14. The support fixture 18, is made from plastic in the preferred embodiment, and includes a backing strip 19 with a back surface which attaches to the foam strip 12, and a support tab 24 which extends substantially perpendicular from the support fixture 18.

Support tab 24 is arcuate in shape to accommodate positioning of an ETT 28 against the lower surface 25 of the support tab 24. Support tab 24 also includes a lip 32 along the distal end to prevent dislodgement of an attachment strip 30 secured to the support tab 24. The strip of adhesive tape 30 is placed along the channel 60 (see FIG. 9) formed by the support tab 24, with a first half of the tape strip 34 extending from the left side of the front of support tab 24 and a second half of tape strip 36 extending from the right side of the front of support tab 24. Tape strip 30 is wrapped around the ETT 28 in order to firmly secure it in place against support tab 24. The lip 32 thereby prevents the tape strip 30 from slipping off the front edge of support tab 24. While the adhesive tape strip is preferred, the attachment strip may be made from hook & pile "VELCRO" strap, adjustable hose style clamp strap, tie strap, and so forth, all of which are deemed within the scope of this invention.

Figure 7:
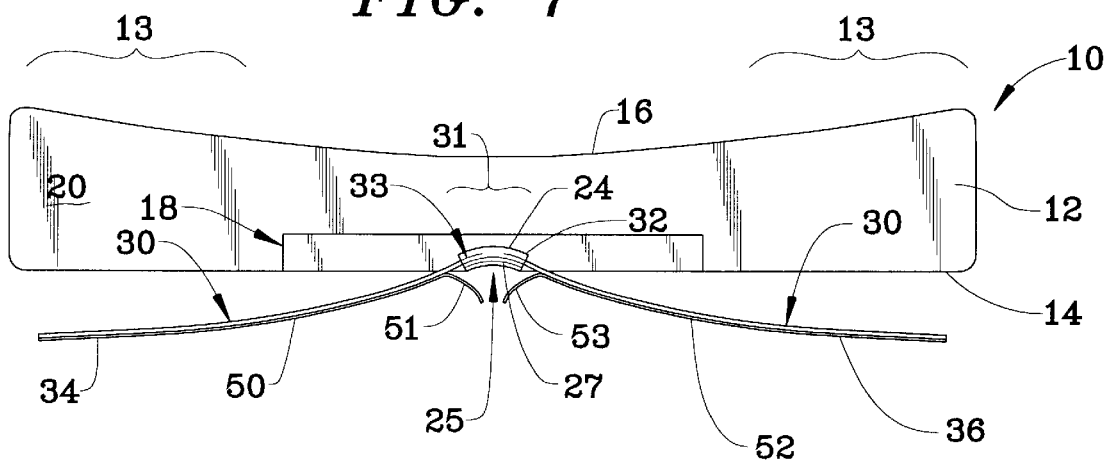
FIG. 7 is a front view of the ETT holder.

Referring also now to FIG. 2, a perspective view is shown of the ETT holder 10 as used with a patient 40 being ventilated with an ETT 28. The foam strip 12 is shaped so that it can be conveniently placed along the upper, or lower, lip of the patient 40, with each widened end of the strip 12 secured to the cheeks 44 of the patient via a medical-grade skin adhesive on the back surface 22 (see FIG. 1, 8 and 9) of the foam strip 12. The ETT 28 is inserted into the mouth 46 of the patient 40, and the support fixture 18 with its backing strip 19 and support tab 24 are shown extending out over the upper lip 42. The arcuate underside 25 of support tab 24 (as shown in FIG. 7) is shaped to approximately conform to the tubular shape of the ETT 28 to more securely hold the ETT 28 in place. The underside has a plurality of ridges, not shown, which frictionally engage the ETT 28 to prevent slippage.

In the illustration shown in FIGS. 1 and 2, the tape strip 30 is adhesively wrapped around the ETT 28 and wherein the left side 34 of the tape strip is placed around the ETT 28 and the right side tape strip 36 is then adhesively wrapped around the ETT 28, as well as the already adhered sections of tape 34. The tape strip secures the ETT 28 in an outward extending and centered position in the patient's mouth 46. The support fixture 18 with extended support tab 24 provides a semi-flexible, yet stable mounting platform for the ETT 28. The foam strip 12 provides a comfortable attachment device which secures the ETT holder 10 to the patient's face 40.

Figure 3:
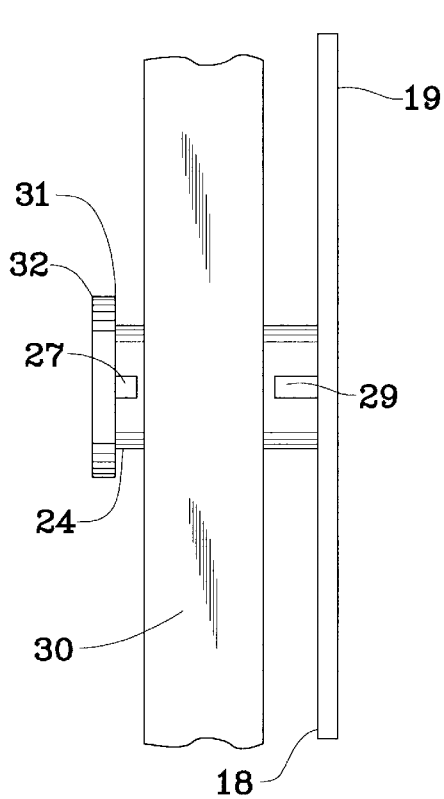
FIG. 3 is a partial top view of the ETT holder illustrating accessory ports.
Figure 4:
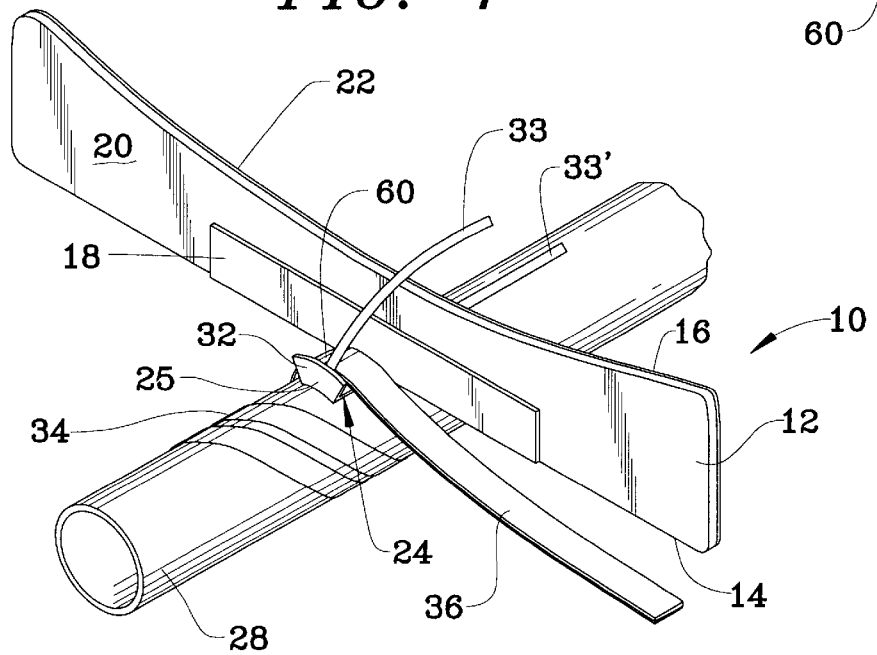
FIG. 4 is a perspective view of the ETT holder having a nasal gastric tube placed through an accessory port.

FIGS. 3 and 4 illustrate the ETT holder 10 with the foam strip 12 having a straight bottom edge 14 and an arcuate shaped upper edge 16. The foam strip 12 includes a front surface 20 and an adhesively backed rear surface 22. A support fixture 18 is adhesively mounted by a backing strip 19, glue or other such substance, to the front surface 20 of the foam strip 12 along the center of the bottom edge 14. Support tab 24 is arcuate in shape to accommodate positioning of the ETT 28 against the lower surface 25 of the support tab 24. Lip 32 is illustrated along the distal end of the tab with accessory ports 27 and 29 positioned along each edge of the support for insertion of accessory tubes such as oral and nasal gastric tubes. Oral gastric tube 33 is shown placed through accessory port 27 wherein it is just positioned against ETT 28 and directed downward with the ETT as depicted by numeral 33'. The bend of the oral gastric tube 33 beneath the support tab 24 causes frictional engagement to prevent movement. The strip of adhesive tape 30 placed along the channel formed by the support tab 24 and lip 32 maintains the tube 33 in position. Preferably the tape is sized to be placed between accessory ports 27 and 29 to allow for ease of tube insertion and wrapping of the tape without interfering with the accessory port location. The lip 32 serves to prevent the tape strip 30 from slipping off the front edge of support tab 24. Locking tab 31 is placed along an upper edge of front lip 32 to prevent the tape strip 30 from slipping. The tab 31 provides a lock for the tape 30 so it cannot be slid over the top of the holder and interfere with the patients comfort. It is noted that all attachment strips are replaceable allowing the device to be reused or repositioned if necessary.

Figure 5:
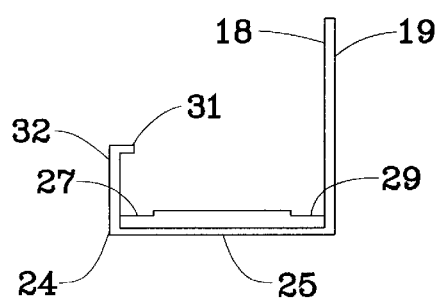
FIG. 5 is a side view of the support tab with accessory ports.
Figure 6:
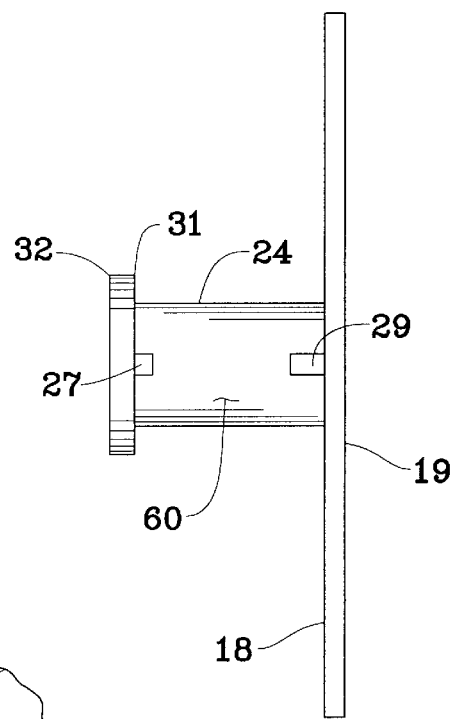
FIG. 6 is a top view of FIG. 5.

Referring also now to FIGS. 5 and 6, the support tab 24 is shown with accessory ports 27 and 29. The accessory ports are spaced apart allowing for the positioning of the attachment tape in the channel formed between the front lip 32 and backing strip 19. The arcuate underside 25 of support tab 24 (also see FIG. 7) is shaped to approximately conform to the shape of the ETT to more securely hold the ETT in place. In addition, the arcuate shape positions the tubes placed through the accessory ports to parallel the ETT wherein the frictional engagement between the tubes eliminates the need for separate securement of the tubes placed through the accessory ports.

Referring also now to FIG. 7, a front view of the ETT holder 10 is shown. The support fixture 18 is adhered via the backing strip 19 to the front surface 20 of the foam strip 12 along the center of the bottom edge 14. The upper edge 16 is arcuate shaped with relatively wider ends 13. The tape strip 30 is adhesively positioned on the arcuately shaped upper surface channel 60 of support tab 24, shown in phantom line. Also shown in phantom line is the plurality of ridges 27 which frictionally engage the ETT 28 to prevent slippage. The left side portion 34 and the right side portion 36 of the tape strip 30 each includes a protective peel-away covering strip 50, 52 placed along the downward facing left and right sides 34, 36 of tape strip 30.

A grasping or pull tab 51, 53 is located on each covering strip 50, 52 along the central portion of the tape strip 30 where the strip 30 adheres to support tab 24. This arrangement allows the user to grasp the ETT holder 10 with one hand and alternate between peeling away the protective coverings 50, 52 for each left and right side 34, 36 of the tape strip 30 with the other hand. Moreover, a central portion 31 of the tape 30 can be first exposed by peeling back and forming grasping or pull tabs 51, 53, with the exposed portion thereafter adhered to the channel 60 of the arcuate-shaped support tab 24. The pull tabs 51, 53 would then flex back over the lower surface 25 of support tab 24 for convenient future access by the user.

Figure 8:
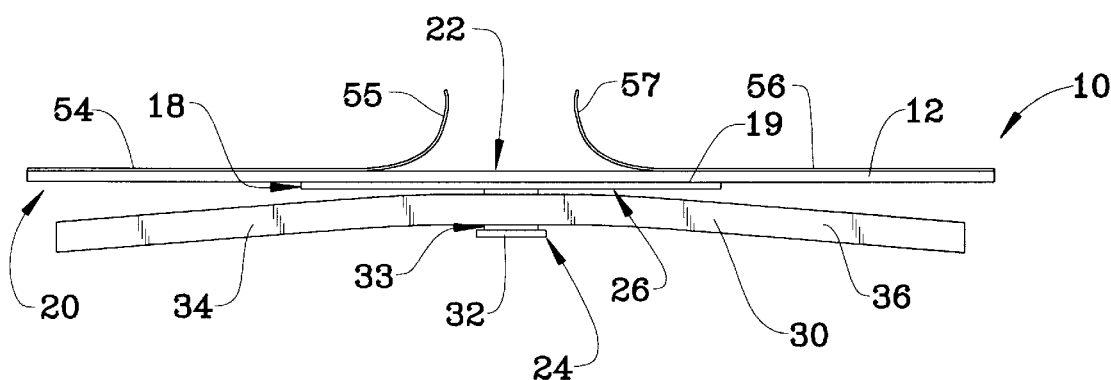
FIG. 8 is an angled rear view of the ETT holder.

Referring to FIG. 8, a top view of the ETT holder 10 is shown. As above, support fixture 18 is attached via backing strip 19 to the center portion of front surface 20 of foam strip 12. Support tab 24 extends outward substantially perpendicular to the front 26 of the backing strip 19. Lip 32 forms a channel 60 (see FIG. 9) for receivably containing the attached adhesive tape strip 30 which is placed along the upper surface 60 of support tab 24. A medical-grade adhesive such as MASTISOL or BENZOIN is applied to the skin where the foam strip 12 attaches to the face and covered with protective covering strips 54 and 56.

The strips 54, 56 include respective pull tabs 55, 57 for grasping and peeling away the strips and exposing the underlying adhesive. As similar to the protective strips 50, 52 for tape 30 described above, strips 54, 56 peel outward from the center portion of the strip 12. Again, this facilitates grasping the device 10 with one hand and alternating removal of the first strip 54 and second strip 56 before positioning and adhesively attaching the ETT holder 10 to the patient's face.

Figure 9:
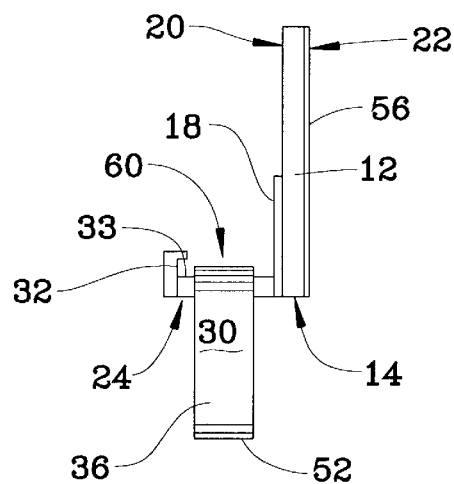
FIG. 9 is a side view of the ETT holder without accessory ports.

Referring now to FIG. 9, a side view of the ETT holder 10 is shown. As above, support fixture 18 is attached to the front surface 20 of foam strip 12, with the bottom surface of fixture 18 aligned along the bottom edge 14 of foam strip 12. Protective strip 56 is shown covering the adhesively backed surface 22 on the rear of foam strip 12. Lip 32 extends up from arcuate surface 60 of support tab 24 forming a channel for receivably containing the adhesive tape strip 30. In this view, the right tape strip portion 36 is shown extending down from support tab 24. The covering strip 52 is slightly oversized so as to completely cover the downward folding adhesive side of the tape strip 30.

Referring now to the Figures collectively, in operation the ETT holder 10 can be attached to the patient either before or after the ETT 28 is inserted into the patient's mouth and down into the trachea. The preferred manner would be to first insert the ETT 28 into a patient as needed. An attending person, e.g. a doctor, respiratory therapist, or nurse would then remove a first and second covering strip 54, 56 from the back of the foam strip 12. This can be done with a single free hand while the ETT 28 and ETT holder 10 are held tandomly in place by the other hand. As each covering strip 54, 56 is removed, the foam strip 12 can be adhered to the patient's face, positioned along the patient's upper or lower lip and attached at each end to the patient's cheeks. The ETT 28 is then oriented to rest against the arcuate cavity surface 25 on the underside of support tab 24. Still, with only one free hand, the adhesive underside of the tape strip 30 is exposed on both the left and right side portions 34, 36 by alternating the peeling away the protective covering strips 50, 52 via the tabs 51, 53. First one side is exposed and wrapped around the ETT 28. Thereafter, the other side is exposed and wrapped around the ETT 28, as well as the tape that is already in place around the ETT 28.

Accordingly, the ETT 28 is securely held in a predisposed position inside the patient, with minimal discomfort due to the foam strip 12 which adheres to a relatively wide area of the patient's face. The foam strip in conjunction with the support fixture 18 with its support tab 24 together allow for stable attachment of the ETT 28 to the foam strip 12. As such, little localized pinching and binding occurs because the stresses encountered by any relative movement of the ETT 28 are distributed evenly over a wide area of the patient's face. Alternatively, the ETT holder 10 could be attached to the patient before inserting the ETT 28 into the patient's mouth and trachea. The ETT 28 would thereafter be secured to the ETT holder 10 as already described.

The ETT holder 10 of the present invention can be conveniently used by a single operator in order to securely anchor an ETT which is either currently in place, or has yet to be inserted in a patient. While securely positioning the ETT for optimum ventilation of the patient, the device also allows for a certain degree of relative movement of the ETT to facilitate patient comfort, but without comprising patient safety. While the embodied device has been described for use with an ETT inserted into a patient's mouth and down into the patient's trachea, the embodied device can also readily be used to hold other such tubes in place, either in a patient's mouth, or elsewhere. Where an attachment surface exists for the foam strip, a tube can be positioned and held by the support fixture and lipped support tab via the tape strip wrapping means.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown in the drawings and descriptions.

What is claimed is:

1. An endotracheal tube (ETT) holding apparatus for securely holding an ETT in position inside a patient, said apparatus comprising:

a facial attachment strip having a front and back surface, an upper and lower edge, and opposite end portions, said back surface including adhesive;

a support fixture having a mounting surface attached to said front of said facial attachment strip and a support tab extending substantially perpendicular from said mounting surface, said support tab having an upper and lower surface and a distally formed lip, said tab being narrower than said mounting surface, said support tab including an aperture providing an accessory port for temporary securement of items inserted above or below the ETT tube;

and a means for securing an ETT to said support tab.

2. The ETT holding apparatus of claim 1, wherein said facial attachment strip is constructed of foam.

3. The ETT holding apparatus of claim 1, wherein said upper edge of said facial attachment strip is arcuate-shaped with end portions which are relatively wider than a center portion, whereby said center portion of said facial attachment strip attaches to the upper or lower lip of a patient and said end portions attach to the patient's cheeks.

4. The endotracheal tube holding apparatus of claim 1, wherein said adhesive on said facial attachment strip back surface is removably covered peel-away protective covering strips.

5. The ETT holding apparatus of claim 3, wherein said protective covering strips have pull tabs along said center portion of said facial attachment strip, said protective covering strips oriented to peel-away towards said end portions.

6. The ETT holding apparatus of claim 1, wherein said support tab includes an arcuate-shaped lower surface, whereby said ETT is positioned to fit within said arcuate-shape which provides a stable guiding and mounting platform.

7. The ETT holding apparatus of claim 6, wherein said arcuate-shaped lower surface includes a plurality of ridges to frictionally engage said ETT.

8. The ETT holding apparatus of claim 6, wherein said support tab includes an arcuate-shaped upper surface and arcuate-shaped distal lip.

9. The ETT holding apparatus of claim 1, wherein said mounting surface and said lip form a channel on said upper surface of said support tab; said means for securing includes at least one tape strip disposed on said support tab; and said channel receivable contains said tape strip, whereby said channel prevents said tape strip from slipping from said support tab.

10. The ETT holding apparatus of claim 4, wherein said facial strip includes a flexible strip with first and second ends which extend from each side of said support tab, said flexible strip having an upper and lower surface, said lower surface having an adhesive backing which is covered by protective covering strips along each said flexible strip end.

11. The ETT holding apparatus of claim 10, wherein said protective covering strips include pull tabs formed along said support tab oriented to peel-away said protective covering strips.

12. The ETT holding apparatus of claim 1, wherein said support tab includes a locking tab formed integral to said support tab to prevent movement of said means for securing.

13. A method of using the ETT holding apparatus of claim 1 by a sole operator with two free hands, including the steps of:

inserting and positioning an ETT inside the patient's mouth and down into the patient's trachea, orienting said lower surface of said support tab of said ETT holding apparatus against said ETT with the operator's first hand;

adhesively adhering said facial attachment strip to the patient's upper lip or lower lip and cheeks with the operator's second hand;

wrapping said tape strip means about said ETT with the operator's second hand, thereby securing said ETT to said support tab.

14. The method of claim 13, wherein said support tab includes an arcuate-shaped lower surface, whereby said ETT is positioned to fit within said arcuate-shape which provides a stable guiding and mounting platform.

15. The method of claim 13, wherein said backing strip and lip form a channel on said upper surface of said support tab, said channel receivable containing said tape strip means from slipping from said support tab.

16. The method of using the ETT holding apparatus of claim 1 by a sole operator with two free hands, including the steps of:

inserting and positioning an ETT inside the patient's mouth and down into the patient's trachea:

peeling away said protective covering strips from said facial attachment strip with the operator's second hand adhering said central portion of said facial attachment strip along the patient's upper or lower lip with said end portions attached to the patient's cheeks, peeling away said protective covering strip from said first flexible strip end and adhesively wrapping said first flexible strip end around said ETT;

peeling away said protective covering strip from said second flexible strip end and adhesively wrapping said second flexible strip end around said ETT.

17. The method of claim 16, wherein said support tab includes an arcuate-shaped lower surface, whereby said ETT is positioned to fit within said arcuate-shape which provides a stable guiding and mounting platform.

18. The method of claim 16, wherein said backing strip and lip form a channel on said upper surface of said support tab, said channel receivable containing said tape strip means from slipping from said support tab.

19. An endotracheal tube (ETT) holding apparatus for securely holding an ETT in position inside a patient, said apparatus comprising:

a facial attachment strip having a front and back surface, an upper and lower edge, and opposite end portions, said back surface including adhesive;

a support fixture having a mounting surface attached to said front of said facial attachment strip and a support tab extending substantially perpendicular from said mounting surface, said support tab having an upper and lower surface and a distally formed lip, said tab being narrower than said mounting surface, said support tab including a locking tab formed integral to said support tab to prevent movement of said means for securing; and a means for securing an ETT to said support tab.

* * * * *